(12) United States Patent
Herrick

(10) Patent No.: US 8,101,581 B2
(45) Date of Patent: Jan. 24, 2012

(54) USE OF D-RIBOSE TO TREAT CARDIAC ARRHYTHMIAS

(75) Inventor: James D. Herrick, Golden Valley, MN (US)

(73) Assignee: Bioenergy, Inc., Ham Lake, MN (US)

( * ) Notice: Subject to any disclaimer, the term of this patent is extended or adjusted under 35 U.S.C. 154(b) by 540 days.

(21) Appl. No.: 12/009,933

(22) Filed: Jan. 23, 2008

(65) Prior Publication Data

US 2008/0176809 A1    Jul. 24, 2008

Related U.S. Application Data

(60) Provisional application No. 60/881,940, filed on Jan. 23, 2007.

(51) Int. Cl.
*A61K 31/7004* (2006.01)
*C07H 3/02* (2006.01)

(52) U.S. Cl. ..................................... 514/23; 536/1.11

(58) Field of Classification Search .................. None
See application file for complete search history.

(56) References Cited

U.S. PATENT DOCUMENTS

| | | | |
|---|---|---|---|
| 4,605,644 A | 8/1986 | Foker | |
| 4,719,201 A | 1/1988 | Foker | |
| 4,824,660 A | 4/1989 | Angello et al. | |
| 6,159,942 A | 12/2000 | St. Cyr et al. | |
| 6,159,943 A | 12/2000 | Butler et al. | |
| 6,218,366 B1 | 4/2001 | St. Cyr et al. | |
| 6,339,716 B1 | 1/2002 | Sawada et al. | |
| 6,429,198 B1 | 8/2002 | St. Cyr et al. | |
| 6,511,964 B2 | 1/2003 | Butler et al. | |
| 6,525,027 B2 | 2/2003 | Vazquez et al. | |
| 6,534,480 B2 | 3/2003 | St. Cyr et al. | |
| 6,548,483 B2 | 4/2003 | Hageman et al. | |
| 6,663,859 B2 | 12/2003 | Percival et al. | |
| 6,703,370 B1 | 3/2004 | Butler et al. | |
| 6,790,603 B2 | 9/2004 | Ericson et al. | |
| 7,094,762 B2 | 8/2006 | Butler et al. | |
| 7,553,817 B2 | 6/2009 | Butler et al. | |
| 2002/0065232 A1 | 5/2002 | Butler et al. | |
| 2002/0119933 A1 | 8/2002 | Butler et al. | |
| 2003/0108537 A1* | 6/2003 | Pola | 424/94.1 |
| 2003/0212006 A1 | 11/2003 | Seifert et al. | |
| 2003/0217577 A1 | 11/2003 | Seifert et al. | |
| 2004/0229204 A1 | 11/2004 | St. Cyr et al. | |
| 2004/0229205 A1 | 11/2004 | Ericson et al. | |
| 2005/0277598 A1 | 12/2005 | MacCarter et al. | |
| 2007/0105787 A1 | 5/2007 | St. Cyr et al. | |
| 2007/0111191 A1 | 5/2007 | St. Cyr et al. | |
| 2008/0146514 A1 | 6/2008 | Verlaan et al. | |
| 2008/0312169 A1 | 12/2008 | Johnson et al. | |
| 2009/0197818 A1 | 8/2009 | St. Cyr et al. | |
| 2009/0197819 A1 | 8/2009 | Johnson et al. | |
| 2009/0232750 A1 | 9/2009 | St. Cyr | |
| 2009/0286750 A1 | 11/2009 | Kasubick et al. | |
| 2010/0009924 A1 | 1/2010 | Butler et al. | |
| 2010/0055206 A1 | 3/2010 | St. Cyr et al. | |
| 2010/0099630 A1 | 4/2010 | MacCarter et al. | |

FOREIGN PATENT DOCUMENTS

| | | | |
|---|---|---|---|
| DE | 19650754 A1 | * | 10/1998 |
| RU | 2 127 548 C1 | | 3/1999 |
| WO | WO 94/04158 A | | 3/1994 |
| WO | WO2007/073178 | * | 6/2007 |
| WO | WO 2008/091618 A1 | | 7/2008 |

OTHER PUBLICATIONS

Machine Translation of DE19650754, published Oct. 6, 1998.*
Watson et al., "Management of Atrial Fibrillation" (2006) Herz vol. 31 pp. 849-856.*
Liu, Pinghuai, "Research of Anti-myocardial Ischemia and Anti-Arrhythmia Cordis Effect of D-Ribose" Zhonggua Yaoye (2005) vol. 14 No. 10 pp. 26-28.*
Chen et al., "Initiation of Atrial Fibrillation by Ectopic Beats Originating From the Pulmonary Veins : Electrophysiological Characteristics, Pharmacological Responses, and Effects of Radiofrequency Ablation" Circulation (1999) vol. 100, pp. 1879-1886.*
International Preliminary Report on Patentability and Written Opinion for PCT/US2008/00845 (11 pgs).
Liu, Pinghuai et. al. Research of anti-myocardial ischemia and anti-arrhythmia cordis effect of D-ribose. Zhongguo Yaoye (2005), 14(10), 26-28.
Zimmer, HG et.al. Ribose accelerates the repletion of the ATP pool during recovery from reversible ischemia of the rat myocardium. J Mol Cell Cardiol (1984), 16:863-866.
Schneider, Hans-Jurgen et. al. D-ribose improves cardiac contractility and hemodynamics. Int J Cardiol (2008) 125(1):49-56.
U.S. Appl. No. 12/583,430, filed Aug. 20, 2009, St. Cyr et al.
U.S. Appl. No. 12/864,408, filed Jul. 23, 2010, Foker.
"Atrial fibrillation," Wikimedia Foundation, Inc., San Francisco, CA, retrieved from the internet at <URL:http://en.wikipedia.org/wiki/Atrial_fibrillation> on Jul. 26, 2010; page last modified on Jul. 26, 2010; 17 pgs.
Liu, Pinghuai et al., "Research of anti-myocardial ischemia and anti-arrhythmia cordis effect of D-ribose," Zhongguo Yaoye, 2005;14(10):26-28, English language translation (7 pgs).

* cited by examiner

*Primary Examiner* — Eric S Olson
(74) *Attorney, Agent, or Firm* — Mueting, Raasch & Gebhardt, P.A.

(57) ABSTRACT

D-ribose, given in doses of five to 15 grams daily, reduces or prevents the occurrence of atrial fibrillation in persons experiencing atrial fibrillation.

3 Claims, No Drawings

USE OF D-RIBOSE TO TREAT CARDIAC ARRHYTHMIAS

RELATED APPLICATIONS

This application claims priority of U.S. Provisional Application 60/881,940, filed Jan. 23, 2007.

BACKGROUND OF THE INVENTION

The heart, like other muscles, is caused to contract by electrical stimulation by nerve fibres. The normal electrical conduction system allows the nerve impluse that is generated by the sinoatrial node of the heart to be propagated to and stimulate the myocardium to contract in an orderly progression, resulting in an efficient heart beat. When the nerve impulses proceed in the normal functional manner, the heart is said to be eurhthymic. When the nerve impulses are reduced or non-uniform the heart is said to be arrhythmic. Arrhythmias may be paroxysmal, that is, acute and short lasting, or chronic.

Extrasystole, or skipped beat, is generally an acute, recurrent event which can be caused by underlying heart disease, valve defects, or may be induced by triggers such as caffeine, nicotine or alcohol. Extrasystole can be felt as "palpitations" and although disturbing, is not, in itself dangerous. Therapy comprises treatment of an underlying heart condition and avoidance of triggers.

Tachycardia is an increased heart rate and can be caused by any trigger that raises the adrenaline levels, such as stress, exercise, strong emotion, caffeine or amphetamine. Heart rate returns to normal as the condition subsides. A severe form of arrhythmia is paroxysmal tachycardia, in which the ventricles contract rapidly and for a prolonged time in the absence of triggers or after the trigger has subsided. The condition is difficult to treat and can be fatal, as the ventricles may pass into fibrillation, in which the blood pressure drops to zero and circulation is halted. Immediate intervention with a defibrillating machine is necessary to preserve life.

Atrial fibrillation is a less serious occurrence. When the atria quiver in fibrillation, blood is not passed to the ventricles efficiently. Circulation is not generally impaired if the period of fibrillation is short; however, the stagnated pool of blood may clot and the clots may be passed to the pulmonary circulatory bed, the coronary arteries, the brain or other organs. It is estimated that about 2.2 million Americans suffer from atrial fibrillation and about 15% of strokes are related to this condition. Paroxysmal atrial fibrillation may have vague symptoms of unease during an attack or the subject may be completely unaware of the condition. Diagnosis is made by the absence of the P wave, representing depolarization of the atria, on EKG.

Atrial fibrillation may be treated with medications which slow the heart rate, "thinning" the blood with aspirin or warfarin to protect the patient from clotting, controlling the heart rate with beta blockers, calcium channel blockers or cardiac glycoside. Electrocardioversion may give persistent normalizing results.

The need remains for a simple treatment with no side effects to help control arrhythmias.

SUMMARY OF THE INVENTION

It has been discovered by this Applicant that D-ribose, in low doses, treats atrial fibrillation and prevents its occurrence partially or completely. Administration of five grams of D-ribose daily, taken as a single dose or divided into two doses is effective at preventing atrial fibrillation. More preferably, ten grams of D-ribose daily, divided into two to four doses is effective at preventing atrial fibrillation. Most preferably, the subject ingests 15 grams of D-ribose daily, divided into at least three doses. No more than five grams of D-ribose is ingested in one dose.

The D-ribose may be taken in a small amount of water, sprinkled on food, or ingested as a powder.

DETAILED DESCRIPTION OF THE INVENTION

The use of D-ribose to improve the function of skeletal and heart muscle has been documented. U.S. Pat. No. 6,159,943 teaches that D-ribose can relieve the cramps and soreness in skeletal muscle caused by exercise. Pending U.S. patent application Ser. No. 10/692,388 teaches that low doses of D-ribose can improve the cardiac function of patients suffering from congestive heart failure. While the use of D-ribose for improving the function of skeletal and cardiac muscle is now well known, before this invention nothing was known of the effect of D-ribose on nerve function. Not wishing to be bound by theory, Applicant speculates that the beneficial effect of D-ribose found in the following study may be due to improving the transmission of the nerve impulses.

Eight patients with a diagnosis of atrial fibrillation were administered D-ribose. The results are tabulated below.

TABLE I

| Patient # | duration of AT | amount of D-ribose daily | other medications | Relief? |
| --- | --- | --- | --- | --- |
| 1. | Recent | N/R* | CoQ | complete, immediate |
| 2. | N/R | N/R | N/R | complete, immediate |
| 3. | N/R | 5 grams | N/R | "helped" |
| 4. | N/R | 5 grams | | complete, within two weeks |
| 5. | 20 years | 10 grams | CoQ, L-carnitine, Mg | complete, immediate |
| 6. | N/R | 10-15 grams | N/R | "practically nonexistent" |
| 7. | N/R | 5 grams | N/R | complete, immediate |

*N/R = not reported

It can be seen from the above data that not all patients are completely and immediately relieved of atrial fibrillation. Patients 5 and 6, all of whom ingested the more preferred and most preferred doses of D-ribose had complete and immediate relief. Patients 3 and 4 had only partial relief (3) or delayed relief (4). Therefore, it is recommended that patients ingest 10 to 15 grams of D-ribose daily.

The relief has persisted for more than a year. Therefore, since there are no side effects from the administration of low doses of D-ribose, it is suggested that use should be continued long term or chronically. While 15 grams daily has been shown to be most effective, larger amounts of D-ribose, up to 30 grams a day may be ingested, provided that no one dose exceeds eight grams, preferably five grams. It has been seen in other studies, as discussed more thoroughly in the '388 application, that many people experience flatulence and diarrhea at doses over about eight grams. Most people tolerate a dose of five grams, which is efficacious for the use taught herein, without experiencing these digestive symptoms.

I claim:

1. A method of treating atrial fibrillation comprising administering an effective amount of D-ribose to a person experiencing atrial fibrillation, wherein the D-ribose is given in daily doses of five to 30 grams.

2. The method of claim 1 wherein the D-ribose is given in daily doses of ten to 15 grams.

3. A method of treating atrial fibrillation comprising administering an effective amount of D-ribose to a person experiencing atrial fibrillation, wherein the D-ribose is given in single doses not exceeding eight grams.

* * * * *